United States Patent
Chewter et al.

(10) Patent No.: US 6,878,851 B2
(45) Date of Patent: Apr. 12, 2005

(54) PROCESS FOR THE HYDROGENATION OF ACETONE

(75) Inventors: Leslie Andrew Chewter, Amsterdam (NL); Wilhelmus Cornelis Nicolaas Dekker, Amsterdam (NL); Stephane Jean Pierre Lecrivain, Amsterdam (NL); Andrew Neave Rogers, Amsterdam (NL)

(73) Assignee: Shell Oil Company, Houston, TX (US)

( * ) Notice: Subject to any disclaimer, the term of this patent is extended or adjusted under 35 U.S.C. 154(b) by 13 days.

(21) Appl. No.: 10/294,782

(22) Filed: Nov. 14, 2002

(65) Prior Publication Data

US 2003/0130546 A1 Jul. 10, 2003

(51) Int. Cl.$^7$ ................................................ C07C 29/14
(52) U.S. Cl. ........................................................ 568/881
(58) Field of Search ......................................... 568/881

(56) References Cited

U.S. PATENT DOCUMENTS

| | | | |
|---|---|---|---|
| 2,456,187 A | 12/1948 | Guinot | ........................ 260/690 |
| 4,894,205 A | 1/1990 | Westerman et al. | .......... 422/197 |
| 5,081,321 A * | 1/1992 | Fukuhara et al. | ............ 568/881 |
| 5,160,497 A * | 11/1992 | Juguin et al. | ................ 568/798 |
| 5,495,055 A * | 2/1996 | Rueter | ......................... 568/881 |
| 6,262,307 B1 * | 7/2001 | Freund et al. | ............... 564/416 |
| 6,486,366 B1 * | 11/2002 | Ostgard et al. | .............. 568/863 |
| 2003/0149314 A1 * | 8/2003 | Chewter et al. | ............. 568/955 |
| 2003/0153793 A1 * | 8/2003 | Sakuth et al. | ................ 568/798 |

FOREIGN PATENT DOCUMENTS

EP     0379323 A3     1/1990     ......... C07C/29/145

OTHER PUBLICATIONS

Perry, "Chemical Engineers' Handbook," 5th Ed., pp. 4–20 to 4–22 (1973).*

* cited by examiner

Primary Examiner—Michael L. Shippen

(57) ABSTRACT

A process for the hydrogenation of acetone to prepare isopropanol is provided, wherein the hydrogenation reaction is carried out in a multi-tubular reactor.

23 Claims, 1 Drawing Sheet

PROCESS FOR THE HYDROGENATION OF ACETONE

FIELD OF THE INVENTION

The present invention relates to a process for the hydrogenation of acetone to isopropanol.

BACKGROUND OF THE INVENTION

Isopropanol is a very useful intermediate in organic synthesis as well as a commercially important solvent.

A process for the hydrogenation of acetone to isopropanol is described in EP-A-0379323. The hydrogenation of acetone to isopropanol is an exothermic process. As indicated in EP-A-0379323 too high reaction temperatures will induce excess hydrogenation decomposition of acetone, resulting in reduced yields of isopropanol. This problem is especially present when hydrogenating acetone. When compared with other ketones, acetone has a relatively low boiling point, and therefore, is easily gasified. Excess gasification can lead to hot spots and hydrogenation decomposition of acetone. Especially in the hydrogenation of acetone it is therefore necessary to precisely control the reaction temperature. One often used method to control the reaction temperature is the recycle of reaction product, e.g. isopropanol. Example 7 of EP-A-0379323 describes preheating of the reactant to 77° C. before entering a vertical reactor column having an inner diameter of 38.4 m, whereafter a reaction mixture at 113° C. was obtained from the outlet of the reactor. The reaction solution was divided into two portions. The first portion was taken out of the reaction system as a product. A second portion was fed back into the reactor by means of a recycle pump and combined with acetone to form a feed mixture for reaction. In the line for recycling the second portion a heat exchanger was provided. The reactor interior temperature was maintained at a predetermined temperature by controlling the jacket temperature of the heat exchanger. However, by recycling reaction product, that contains large amounts of isopropanol, the process becomes less economical and the amount of, for example, di-isopropyl ether, a major by-product, can increase. Furthermore the controllability of the temperature in the reactor itself is limited.

SUMMARY OF THE INVENTION

Accordingly a process for the hydrogenation of acetone to prepare isopropanol is provided, wherein the hydrogenation reaction is carried out in a multi-tubular reactor.

DETAILED DESCRIPTION OF THE INVENTION

Figure 1:
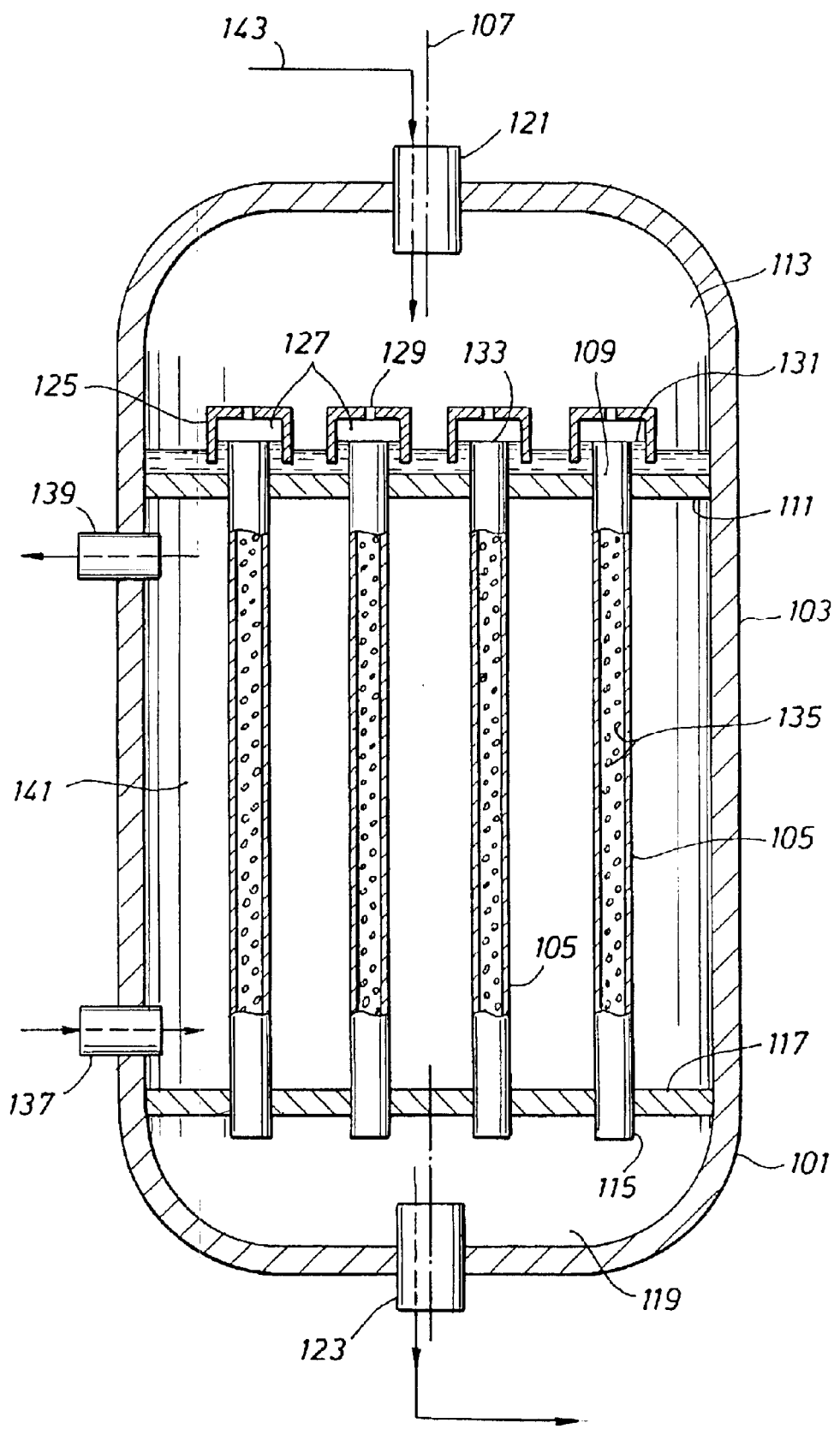
FIG. 1 is an illustrated embodiment of the multi-tubular reactor.

It is desirable to provide an improved process for the hydrogenation of acetone in terms of economics and temperature control. Such an improved process has been found by using a multi-tubular reactor. A process for the hydrogenation of acetone to prepare isopropanol is provided, wherein the hydrogenation reaction is carried out in a multi-tubular reactor.

The use of a multi-tubular reactor enables a more regulated and more controlled removal of reaction heat. Furthermore the process is economically more advantageous because there is no necessity of recycling precious reaction product.

The multi-tubular reactor used in the process according to the invention preferably comprises a substantially vertically extending vessel, a plurality of open-ended reactor tubes arranged in the vessel parallel to its central longitudinal axis of which the upper ends are fixed to an upper tube plate and in fluid communication with a top fluid chamber above the upper tube plate and of which the lower ends are fixed to a lower tube plate and in fluid communication with a bottom fluid chamber below the lower tube plate, supply means for supplying reactants to one of the fluid chambers and an effluent outlet arranged in the bottom fluid chamber.

During operation the reactor tubes are filled with catalyst particles.

To convert acetone and hydrogen into isopropanol, acetone can be supplied through the top fluid chamber into the upper ends-of the reactor tubes and passed through the reactor tubes. Hydrogen can be supplied either through the top fluid chamber (top-down) or through the bottom fluid chamber (bottom-up). Preferably hydrogen is supplied co-currently with the acetone through the top fluid chamber (top-down). Effluent reaction product leaving the lower ends of the reactor tubes is collected in the bottom fluid chamber and removed from the bottom fluid chamber through the effluent outlet.

The heat of reaction is removed by a cooling fluid, which is passed along the outer surfaces of the reactor tubes. A wide range of liquids can be used as cooling fluid. Examples include water and hydrocarbons such as for example kerosene and thermal oil. Water is a preferred cooling fluid.

In a preferred embodiment a multi-tubular reactor such as described in U.S. Pat. No. 4,894,205 is used which disclosure is herein incorporated by reference. In such a multi-tubular reactor the upper end part of each open-ended reactor tube is provided with a gas and liquid supply device, which device comprises an inlet chamber having a gas inlet opening, a liquid inlet and an outlet which is in fluid communication with the upper end part of the reactor tube, and a liquid riser extending between a level in the layer of liquid which is during normal operation present in the top fluid chamber and the liquid inlet of the inlet chamber.

Reactor size will depend on the desired capacity and can vary within wide ranges. Preferably the internal diameter of the reactor lies in the range of 0.1 to 8 m. For example, a reactor with a relatively low throughput of hydrogenated product, e.g. 10 to 30 kilo ton a year, the preferred diameter lies in the range of 0.4 to 1.4 m, for a reactor with a moderate throughput of hydrogenated product, e.g. 30 to 70 kilo ton a year, the preferred diameter lies in the range of 0.7 to 2 m, for a reactor with a large throughput of hydrogenated product, e.g. 70 to 130 kilo ton a year, the preferred diameter lies in the range of 1 to 3 m and for a reactor with a very large throughput of hydrogenated product, e.g. 130 to 200 kilo ton a year, the preferred diameter lies in the range of 1.5 to 5 m. The number of reactor tubes can vary within a wide range and also depends on the desired capacity. For practical purposes a number of reactor tubes in the range from 10 to 20,000 is preferred and a number of reactor tubes in the range of 100 to 10,000 is more preferred.

The internal diameter of the reactor tubes should be small enough to allow the sufficient transfer of reaction heat to the cooling liquid and large enough to avoid unnecessary material costs. The optimal diameter of the reactor tubes is dependent on the amount of reaction heat generated by the hydrogenation process and can vary with the type of reactants, the amount of reactants and the catalyst used. In the process of the present invention reactor tube internal diameters in the range of 10 to 100 mm, more preferably in the range from 20 to 70 mm are preferred.

The hydrogenation process can be performed at a wide range of reaction temperatures. Preferably temperatures applied in the reactor lie in the range from 40–150° C., more preferably in the range from 60–120° C.

The use of a multi-tubular reactor advantageously allows for regulation and control of the reactor temperature. The temperature applied in the reactor can be constant from the top of the reactor tube to the bottom of the reactor tube or can gradually increase or decrease. In a preferred embodiment the hydrogenation process is carried out in a multi-tubular reactor having a decreasing temperature profile. That is, the reactants are supplied to the top of the reactor tube at a high temperature whereas the temperature is gradually decreasing from the top to the bottom of the reactor tube. Such a decreasing temperature profile results in a high conversion and low formation of di-isopropyl ether.

Reaction pressure can vary between wide ranges, but preferably lies in the range from 2 to 100 bar, more preferably in the range from 10 to 40 bar. A higher pressure will result in increased costs whereas a lower pressure can result in poor conversion rates. If acetone is supplied as a liquid, the gas is preferably essentially pure hydrogen, though this hydrogen can contain minor amounts of methane, ethane, nitrogen and other impurities.

The molar ratio of hydrogen to acetone is preferably at least 1. More preferably the molar ratio of hydrogen to acetone lies in the range from 1:1 to 10:1, most preferably in the range from 1.5:1 to 5:1.

The amount of catalyst needed depends on the desired capacity and the activity of the catalyst. Catalyst volumes in the range from 0.1 to 50 $m^3$, preferably in the range from 0.5 to 20 $m^3$, are most practical.

The catalyst used in the process according to the invention can be any catalyst known to be suitable for the hydrogenation of carbonyl compounds (hydrogenation catalysts). Possible catalysts include copper based catalyst such as copper-chromium, Raney copper and copper zinc; nickel based catalysts such as reduced nickel catalysts prepared by carrying nickel oxide on a diatomaceous earth alumina or silica support or Raney nickel catalysts; and platinum group catalysts such as platinum, palladium, ruthenium and rhodium as well as the foregoing catalysts on activated carbon and alumina supports.

In a preferred embodiment a nickel based catalyst is used. More preferably a nickel on silica catalyst is used.

Preferably the catalyst is present in the multi-tubular reactor as a fixed bed.

In an advantageous embodiment the process according to the invention is operated at trickle flow. That is, liquid carbonyl compound trickles along the surface of the catalyst, which is packed in an atmosphere full of hydrogen gas.

A broad range of liquid and gas flows can be used. For practical reasons the superficial gas velocity is preferably in the range of 0.01–10 m/s, and the superficial liquid velocity is preferably in the range of 0.0001–0.1 m/s.

In the process of the invention, the feed of acetone can contain some reaction product. For example, an acetone feed can contain some isopropanol. Preferably, however, the amount of reaction product in the feed is less than 50% w/w, more preferably less than 10% w/w and most preferably in the range from 0 to 5% w/w.

An illustration of a process according to the invention is now described by reference to FIG. 1.

A multi-tubular reactor (101) is used, comprising a substantially vertically extending vessel (103) and a plurality of open-ended reactor tubes (105) (for practical purposes only four of those are depicted in FIG. 1). The open-ended reactor tubes (105) are arranged in the vessel (103) parallel to its central longitudinal axis (107). The upper ends (109) of the open-ended reactor tubes (105) are fixed to an upper tube plate (111) and in fluid communication with a top fluid chamber (113) above the upper tube plate (111). The lower ends (115) of the open-ended reactor tubes (105) are fixed to a lower tube plate (117) and in fluid communication with a bottom fluid chamber (119) below the lower tube plate (117). The vessel comprises supply means (121) for supplying reactants to the top fluid chamber (113) and an effluent outlet (123) arranged in the bottom fluid chamber (119). The upper part of the open-ended reactor tubes is provided with a gas and liquid supply device (125), arranged in the top fluid chamber. This gas and liquid supply device comprises an inlet chamber (127) having a gas inlet opening (129), a liquid inlet (131) and an outlet (133), which is in fluid communication with the upper end part of the open-ended reactor tube. The open-ended reactor tubes (105) are filled with a nickel on silica catalyst (135). The vessel (103) further comprises supply means (137) and an outlet (139) for a cooling liquid, e.g. water, such that a falling temperature profile is obtained. The cooling liquid is supplied to a cooling chamber (141) between the upper tube plate (111) and the lower tube plate (117).

A feed (143) of acetone and hydrogen, preheated to a temperature of for example 100° C. is fed, at a pressure of for example 25 atm into the reactor through the gas and liquid supply device (125) into the open-ended reactor tubes (105) via the top fluid chamber (113). In the open-ended reactor tubes (105) acetone and hydrogen are reacted to isopropanol over the nickel on silica catalyst (135). Reaction effluent, containing amongst others isopropanol and small amounts of di-isopropyl ether, is withdrawn from the open-ended reactor tubes (105) to the effluent outlet (123) via the bottom fluid chamber (119).

We claim:

1. A process for the hydrogenation of acetone to prepare isopropanol, wherein the hydrogenation reaction is carried out in a multi-tubular reactor comprising a substantially vertically extending vessel, a plurality of open-ended reactor tubes arranged in the vessel parallel to its central longitudinal axis of which the upper ends are fixed to an upper tube plate and in fluid communication with a top fluid chamber above the upper tube plate and of which the lower ends are fixed to a lower tube plate and in fluid communication with a bottom fluid chamber below the lower tube plate, supply means for supplying reactants to the top fluid chamber and an effluent outlet arranged in the bottom fluid chamber, the upper end part of each reactor tube is provided with a gas and liquid supply device, which device comprises an inlet chamber having a gas inlet opening, a liquid inlet and an outlet which is in fluid communication with the upper end part of the reactor tube, and a liquid riser extending between a level in the layer of liquid which is during normal operation present in the top fluid chamber and the liquid inlet of the inlet chamber.

2. The process of claim 1 wherein the internal diameter of the reactor lies in the range of 0.1 to 8 m.

3. The process of claim 1 wherein the number of reactor tubes is in the range from 10 to 20,000.

4. The process of claim 3 wherein the internal diameter of the reactor lies in the range of 0.1 to 8 m.

5. The process of claim 1 wherein the reaction tubes have an internal diameter in the range of 10 to 100 mm.

6. The process of claim 3 wherein the reactor tubes have an internal diameter in the range of 10 to 100 mm.

7. The process of claim 4 wherein the reactor tubes have an internal diameter in the range of 10 to 100 mm.

8. The process of claim 1 wherein the hydrogenation is carried out at a temperature in the range from 40 to 150° C.

9. The process of claim 2 wherein the hydrogenation is carried out at a temperature in the range from 40 to 150° C.

10. The process of claim 3 wherein the hydrogenation is carried out at a temperature in the range from 40 to 150° C.

11. The process of claim 5 wherein the hydrogenation is carried out at a temperature in the range from 40 to 150° C.

12. The process of claim 1 wherein the hydrogenation process is carried out in a multi-tubular reactor having a decreasing temperature profile.

13. The process of claim 12 wherein the hydrogenation is carried out at a temperature in the range from 40 to 150° C.

14. The process of claim 3 wherein the hydrogenation process is carried out in a multi-tubular reactor having a decreasing temperature profile.

15. The process of claim 1 wherein the hydrogenation is carried out in the presence of a nickel on silica catalyst.

16. The process of claim 3 wherein the hydrogenation is carried out in the presence of a nickel on silica catalyst.

17. The process of claim 5 wherein the hydrogenation is carried out in the presence of a nickel on silica catalyst.

18. The process of claim 1 wherein the reactor is operated at trickle flow.

19. The process of claim 3 wherein the reactor is operated at trickle flow.

20. The process of claim 4 wherein the reactor is operated at trickle flow.

21. The process of claim 5 wherein the reactor is operated at trickle flow.

22. The process of claim 15 wherein the reactor is operated at trickle flow.

23. The process of claim 1 wherein the acetone used contains less than 50% reaction product.

* * * * *